United States Patent [19]

Sestanj et al.

[11] 4,446,150
[45] May 1, 1984

[54] NAPHTHALENYLTHIAZOLE DERIVATIVES

[75] Inventors: Kazimir Sestanj, St. Laurent; Francesco Bellini, Mount Royal, both of Canada

[73] Assignee: Ayerst, McKenna & Harrison, Inc., Montreal, Canada

[21] Appl. No.: 420,776

[22] Filed: Sep. 21, 1982

[51] Int. Cl.³ .................. C07D 277/34; A61K 31/425
[52] U.S. Cl. .................................... 424/270; 548/182; 548/186
[58] Field of Search .................. 548/182, 186; 424/270

[56] References Cited

U.S. PATENT DOCUMENTS 2,441,558 5/1948 Brooker .............................. 548/182
2,474,426 6/1949 Kendall et al. ...................... 548/182
3,539,585 11/1970 Sulkowski et al. .................. 548/182

FOREIGN PATENT DOCUMENTS 78100053.4 12/1978 European Pat. Off. .

Primary Examiner—Robert Gerstl
Attorney, Agent, or Firm—Arthur E. Wilfond

[57] ABSTRACT

Disclosed herein are new aldose reductase inhibitors of the formula

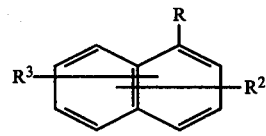

wherein R is

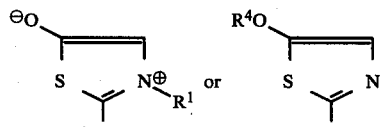

wherein $R^1$ is lower alkyl; $R^2$ is halo and $R^3$ is hydrogen, or $R^2$ and $R^3$ each is a substituent at positions 3, 4, 5 or 6 of the naphthalene ring selected from the group consisting of lower alkoxy, trihalomethyl, and halo; and $R^4$ is lower alkyl. The derivatives are useful for treating or preventing diabetic complications.

10 Claims, No Drawings

NAPHTHALENYLTHIAZOLE DERIVATIVES

BACKGROUND OF THE INVENTION

This invention relates to naphthalenylthiazole derivatives. More specifically, this application relates to 2-(1-naphthalenyl)thiazole derivatives, to processes for their preparation, to methods for using the derivatives, and to pharmaceutical preparations thereof. The derivatives have pharmaceutical properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, cataracts and atherosclerosis. These complications have been linked to the undesirable accumulation of sorbitol in diabetic tissue, which in turn result from the high levels of glucose characteristic of the diabetic patient.

In mammals, including humans, the key enzyme involved in the conversion of hexoses to polyols (e.g. the sorbitol pathway) is aldose reductase. J. H. Kinoshita and collaborators, see J. H. Kinoshita et al., Biochem. Biophys. Acta, 158, 472 (1968) and references cited therein, have demonstrated that aldose reductase plays a central role in the etiology of glactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nervous cord and kidney of diabetic animals, see A. Pirie and R. van Heyningen, Exp. Eye Res., 3, 124 (1964); L. T. Chylack and J. H. Kinoshita, Invest. Ophthal., 8, 401 (1969) and J. D. Ward and R. W. R. Baker, Diabetol., 6, 531 (1970).

1,3-Dioxo-1H-benz[de]isoquinoline-2(3H)-acetic acid has been reported to be an effective inhibitor of aldose reductase, see D. Dvornik et al., Science, 182, 1146 (1973), and to be useful for the treatment of diabetic complications such as diabetic cataracts, neuropathy, nephropathy and retinopathy, see K. Sestanj, N. Simard-Duquesne and D. M. Dvornik, U.S. Pat. No. 3,821,383, June 28, 1974. Other compounds having a similar utility are the thioxo-1H-benz[de]isoquinoline-2(3H)-acetic acid derivatives of K. Sestanj, U.S. Pat. No. 4,254,108, Mar. 3, 1981 and 1H-benz[de]isoquinoline-2(3H)-acetic acid derivatives of K. Sestanj, U.S. Pat. No. 4,254,109, Mar. 3, 1981. Still other compounds having a similar utility are 2-thioxobenz[c,d]indole-1(2H)-acetic acid derivatives of K. Sestanj, U.S. patent application Ser. No. 284,049, filed July 17, 1981; N-naphthoylglycine derivatives of K. Sestanj et al., U.S. patent application Ser. No. 321,306, filed Nov. 13, 1981; N-(Naphthalenylthioxomethyl)amino acid derivatives of K. Sestanj et al., U.S. patent application Ser. No. 321,304, filed Nov. 13, 1981; N-[(2-naphthalenyl)thioxomethyl]glycine derivatives of K. Sestanj, U.S. patent application Ser. No. 321,303, filed Nov. 13, 1981; and N-[[6-(lower alkoxy)-5-(trifluoromethylthio)-1-naphthalenyl]thioxomethyl]-N-(lower alkyl)-glycines of F. Bellini et al., U.S. patent application Ser. No. 321,300, filed Nov. 13, 1981. (S)-6-Fluoro-2,3-dihydrospiro(4H-1-benzopyran-4,4'-imidazolidine)-2',5'-dione(sorbinil) is still another compound that has received attention because of its aldose reductase inhibiting properties (see M. J. Peterson et al., Metabolism 28 (Suppl. 1), 456 (1979). Accordingly, these compounds represent an important new approach for the treatment of diabetes mellitus.

The present application discloses novel naphthalenylthiazole derivatives, represented below by formula Ia and Ib, which are effective inhibitors of aldose reductase. These new derivatives are structurally quite different from the above noted aldose reductase inhibitors.

Previously reported naphthalenyltriazole derivatives differ from the present derivatives by having completely different substituents, by being at a different oxidation level in some instance, and by having completely different utilities. Typical examples of such naphthalenylthiazole derivatives are disclosed by T. S. Sulkowski and A. A. Mascitti, U.S. Pat. No. 3,539,585, Nov. 10, 1970; by J. J. Baldwin and G. Salvatore, European patent application No. 78100053.4, published Dec. 20, 1978 under No. 0 000 032; by L. G. S. Brooker, U.S. Pat. No. 2,441,558, May 18, 1948; and by J. D. Kendale et al., U.S. Pat. No. 2,474,426, June 28, 1949.

SUMMARY OF THE INVENTION

The naphthalenylthiazole derivatives of this invention are represented by formula I

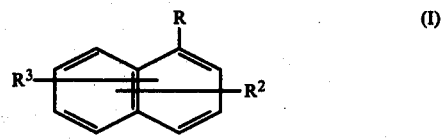

wherein R is

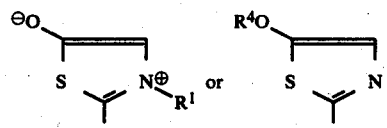

wherein $R^1$ is lower alkyl; $R^2$ is a halo substituent on the naphthalene ring and $R^3$ is hydrogen, or $R^2$ and $R^3$ each is a substituent at positions 3, 4, 5 or 6 of the naphthalene ring selected from the group consisting of lower alkoxy, trihalomethyl and halo; and $R^4$ is lower alkyl.

The naphthalenylthiazoles also can be represented by formulae Ia and Ib

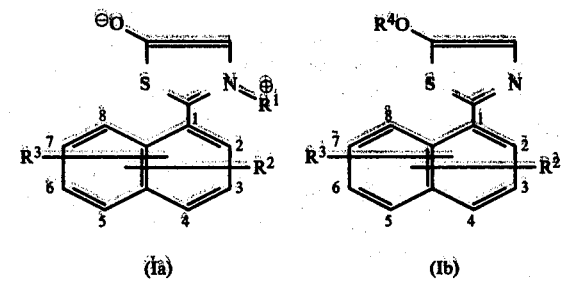

wherein $R^1$, $R^2$, $R^3$ and $R^4$ are as defined hereinabove.

A preferred group of compounds of this invention is represented by formula Ia wherein $R^1$ is lower alkyl; $R^2$ is 5-halo and $R^3$ is hydrogen, or $R^2$ and $R^3$ are a pair of substituents on the naphthalene ring, the pair being selected from the group of pairs consisting of 3-halo-4-lower alkoxy, 5-halo-6-lower alkoxy and 5-(trifluoromethyl)-6-lower alkoxy.

A more preferred group of the compounds of the invention is represented by formula Ia wherein $R^1$ is lower alkyl, $R^2$ is 5-trifluoromethyl and $R^3$ is 6-lower alkoxy.

Another preferred group of the compounds of this invention is represented by formula Ib wherein $R^2$ is 5-halo and $R^3$ is hydrogen, or $R^2$ and $R^3$ are a pair of substituents on the naphthalene ring, the pair of substituents being selected from the group of pairs consisting of 3-halo-4-lower alkoxy, 5-halo-6-lower alkoxy and 5-(trifluoromethyl)-6-lower alkoxy; and $R^4$ is lower alkyl.

Another more preferred group of the compound of this invention is represented by formula Ib wherein $R^2$ is 3-halo, $R^3$ is 4-lower alkoxy and $R^4$ is lower alkyl.

The naphthalenylthiazole derivatives can be prepared by a process described hereinafter.

A method is provided for preventing or relieving diabetes mellitus associated complications in a diabetic mammal by administering to said mammal a prophylactic or alleviating amount of the compound of formula Ia or formula Ib. Such complications include neuropathy, nephropathy, retinopathy and cataracts.

The compound of formula Ia or formula Ib, when admixed with a pharmaceutically acceptable carrier, forms a pharmaceutical compositon which can be used according to the preceding method.

DETAILED DESCRIPTION OF THE INVENTION

The term "lower alkyl" as used herein means a straight chain alkyl radical containing from one to six carbon atoms or a branched chain alkyl radical containing three or four carbon atoms and includes methyl, ethyl, propyl, 1-methylethyl, butyl, 1,1-dimethylethyl, hexyl and 1-ethyl-2-methylpropyl. Preferred lower alkyl radicals contain from one to three carbon atoms.

The term "lower alkoxy" as used herein means a straight chain alkoxy radical containing from one to six carbon atoms, preferably one to three carbon atoms, or a branched chain alkoxy radical containing three or four carbon atoms, and includes methoxy, ethoxy, 1-methylethoxy, butoxy and hexyloxy.

The term "halo" as used herein means a halo radical and includes fluoro, chloro, bromo and iodo.

The term "lower alkanoic acid" as used herein means both straight and branched chain alkanoic acids containing from two to four carbon atoms and includes acetic acid, propanoic acid, 2-methylpropionic acid and the like.

The term "organic proton acceptor" as used herein means the organic bases or amines, for instance, triethylamine, pyridine, N-ethylmorpholine and 1,5-diazabicyclo[4.3.0]non-5-ene.

The naphthalenylthiazole derivatives of this invention may be administered to mammals, for example, man, cattle or rabbits, either alone or in dosage forms, i.e., capsules or tablets, combined with pharmacologically acceptable excipients, see below.

Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the naphthalenylthiazole derivatives will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally affords effective results without causing any harmful or deleterious side effects. For topical administration a 0.05–0.2% solution may be administered dropwise to the eye. The frequency of installation varies with the subject under treatment from a drop every two or three days to once daily. For oral or parenteral administration a preferred level of dosage ranges from about 0.1 mg to about 200 mg per kilo of body weight per day, although aforementioned variations will occur. However, a dosage level that is in the range of from about 3.0 mg to about 30 mg per kilo of body weight per day is most satisfactory.

Unit dosage forms such as capsules, tablets, pills and the like may contain from about 5.0 mg to about 250 mg of the active ingredients of this invention with a pharmaceutical carrier. Thus, for oral administration, capsules can contain from between about about 5.0 mg to about 250 mg of the active ingredients of this invention with or without a pharmaceutical diluent. Tablets, either effervescent or noneffervescent, can contain between about 5.0 to 250 mg of the active ingredients of this invention together with conventional pharmaceutical carriers. Thus, tablets which may be coated and either effervescent or noneffervescent may be prepared according to the known art. Inert diluents or carriers, for example, magnesium carbonate or lactose, can be used together with conventional disintegrating agents for example, magnesium stearate.

The naphthalenylthiazole derivatives also can be used in combination with insulin or oral hypoglycemic agents to produce a beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The naphthalenylthiazole derivative can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference," 36 ed., Medical Economics Co., Oradell, N.J., U.S.A., 1982. When used in combination, the naphthalenylthiazole derivative is administered as described previously. The naphthalenylthiazole derivatives can be administered with the oral hypoglycemic agent in the form of a pharmaceutical composition comprising effective amounts of each agent.

The aldose reductase inhibiting property of the compounds of this invention and the utilization of the compounds in preventing, diminishing and alleviating diabetic complications are demonstrable in experiments using galactosemic rats, see Dvornik et al., cited above. Such experiments are exemplified hereinbelow after the listing of the following general comments pertaining to these experiments:

(a) Four or more groups of six male rats, 50–70 g, Sprague-Dawley strain, were used. The first group, the control group, was fed a mixture of laboratory chow (rodent laboratory chow, Purina) and glucose at 20% (w/w %) concentration. The untreated galactosemic group was fed a similar diet in which galactose is substituted for glucose. The third group was fed a diet prepared by mixing a given amount of the test compound with the galactose containing diet. The concentration of galactose in the diet of the treated groups was the same as that for the untreated galactosemic group.

(b) After four days, the animals were killed by decapitation. The eyeballs were removed and punctured with a razor blade; the freed lenses were rolled gently on filter paper and weighed. The sciatic nerves were dissected as completely as possible and weighed. Both tissues were frozen and can be kept up to two weeks before being analyzed for dulcitol.

(c) The polyol determination was performed by a modification of the procedure of M. Kraml and L. Cosyns, Clin. Biochem., 2, 373 (1969). Only two minor reagent changes were made: (a) The rinsing mixture was an aqueous 5% (w/v) trichloroacetic acid solution and (b) the stock solution was prepared by dissolving 25 mg of dulcitol in 100 ml of an aqueous trichloroacetic acid solution. [N.B.: For each experiment the average value found in the tissue from rats fed the glucose diet was subtracted from the individual values found in the corresponding rat tissue to obtain the amount of polyol accumulated.]

The following tabulated results show that the naphthalenylthiazole derivatives of this invention diminish the accumulation of dulcitol in the lenses and sciatic nerves of rats fed galactose. The figures under L, N and D represent the percentage decrease of dulcitol accumulation in the tissues of the lens, sciatic nerve and diaphragm, respectively, for treated rats as compared to untreated rats.

| Test compound | Dose mg/ kg/ day | L | N | D |
|---|---|---|---|---|
| 2-(5-bromo-1-naphthalenyl)-5-hydroxy-3-methylthiazolium hydroxide, inner salt | 26 | NS | 31 | 32 |
| 5-hydroxy-2-[5-(trifluoromethyl)-6-methoxy-1-naphthalenyl]-3-methyl-thiazolium hydroxide, inner salt | 21.1 | 21 | 70 | 89 |
|  | 9.9 | 14 | 34 | 76 |
|  | 5.1 | NS | NS | 64 |
| 2-(3-chloro-4-methoxy-1-naphthalenyl)-5-ethoxythiazole | 137 | 16 | 28 | NS |

Not Significant

Process

The naphthalenylthiazole derivatives can be prepared by:

(a) cyclizing a compound of formula II

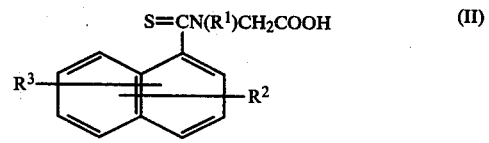

wherein $R^1$ is lower alkyl; $R^2$ is a halo substituent on the naphthalene ring and $R^3$ is hydrogen or $R^2$ and $R^3$ each is a substituent at positions 3, 4, 5 or 6 of the naphthalene ring selected from the group consisting of lower alkoxy, trihalomethyl or halo, in the presence of a lower alkanoic acid anhydride and an organic proton acceptor to obtain the corresponding compound of formula Ia wherein $R^1$, $R^2$ and $R^3$ are as defined herein; or (b) cyclizing a compound of formula III

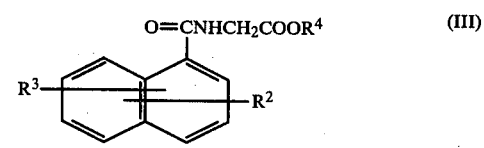

wherein $R^2$ and $R^3$ are as defined herein, and $R^4$ is lower alkyl with phosphorus pentasulfide to obtain the corresponding compound of formula Ib wherein $R^2$, $R^3$ and $R^4$ are as defined herein.

More specifically, the compounds of formula Ia can be obtained by cyclizing a corresponding compound of formula II in the presence of a mixture of at least one molar equivalent of a lower alkanoic acid anhydride, containing from two to four carbon atoms in each acyl portion, and at least one molar equivalent of an organic proton acceptor. Optionally, the cyclization can be performed in an inert organic solvent, e.g. dimethylformamide, tetrahydrofuran or toluene. The cyclization is performed most efficiently under anhydrous conditions, and is performed most conveniently by using the mixture of the alkanoic acid anhydride and the organic proton acceptor as the reaction medium. Preferred conditions include the use of acetic anhydride as the lower alkanoic anhydride, and the use of triethylamine, N-ethylmorpholine or pyridine as the proton acceptor. Although the optimum temperature and reaction time will vary depending on the reactants employed, the reaction usually is completed within ten minutes to two hours at a temperature range of 20° to 60° C.

An analogous cyclization of simple thiocylamino acids to corresponding thiazolium derivatives has been reported by M. A. Elgendy and M. A. Eldawy, J. Pharm. Sci., 17, 35 (1976).

The compounds of formula Ib can be obtained by cyclizing the corresponding compound of formula III under anhydrous conditions with about two to five molar equivalents of phosphorus pentasulfide in an organic solvent, e.g. pyridine, xylene or toluene. The cyclization is performed usually at temperatures ranging from 80° to about 150° C. for 20 minutes to four hours. Preferably, the reaction is done in the presence of an organic proton acceptor; for instance, triethylamine, N-ethylmorpholine or pyridine. Generally, the desired naphthalenylthiazole of formula Ib is obtained along with a byproduct which is the corresponding thioxo analog of the starting material of formula III. The desired compound can be separated from the byproduct by standard laboratory techniques, for instance, crystallization or chromatography. A rapid and convenient method for effecting this separation involves subjecting the mixture to the action of a strong base, e.g. sodium hydroxide or potassium carbonate, in a reaction medium of water and a solvent miscible with water e.g. methanol, ethanol or acetone. Under these conditions, the ester byproduct is hydrolyzed to its corresponding acid which dissolves in the alkaline medium, and the desired naphthalenylthiazole derivative of Ib can be isolated by filtration or by extraction.

An analogous cyclization of simple acylaminoacid esters to corresponding thiazole derivatives has been reported by D. S. Tarbell et al., J. Amer. Chem. Soc., 72, 3138 (1950).

The aforementioned starting materials of formulae II and III are disclosed in copending U.S. patent application Ser. No. 321,306, filed Nov. 13, 1981, herein incorporated by reference. European patent (EPC) application Ser. No. 82300940.2, filed Feb. 24, 1982 and published Sept. 8, 1982, also discloses the starting materials.

A method for the preparation of the starting material of formula II, disclosed in the aforementioned patent applications, is illustrated by the following reaction scheme.

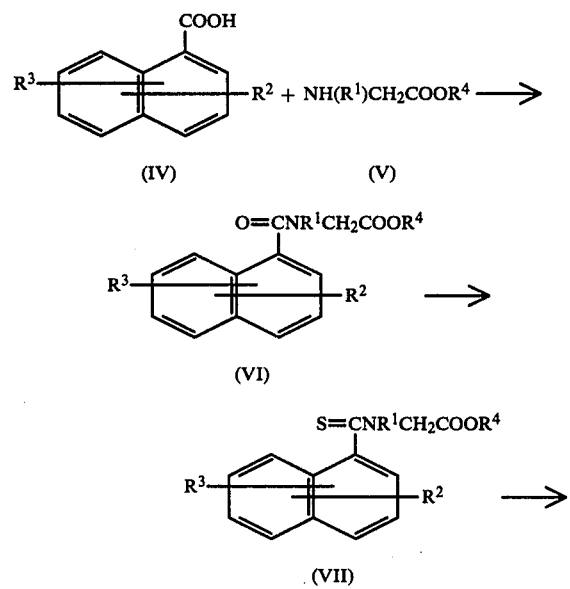

More explicitly, the starting material of formula II is prepared by first coupling a naphthalenecarboxylic acid of formula IV wherein $R^2$ and $R^3$ are as defined herein with an aminoacid ester of formula V wherein $R^1$ and $R^4$ are as defined herein to obtain the corresponding amidoester of formula VI wherein $R^1$, $R^2$, $R^3$ and $R^4$ is as defined herein.

The compounds of formulae IV and V are known or can be prepared by known methods. For example, see "Elsevier's Encyclopaedia of Organic Chemistry," F. Radt, Ed., Series III, Vol. 12B, Elsevier Publishing Co., Amsterdam, 1953, pp 3965–4473. The coupling of the naphthalenecarboxylic acid IV and the amino acid ester V is done preferably by the "carboxyl activation" coupling procedure. Descriptions of carboxyl-activating groups are found in general textbooks of peptide chemistry; for example K. D. Kopple, "Peptides and Amino Acids", W. A. Benjamin, Inc., New York, 1966, pp. 45–51, and E. Schröder and K. Lübke, "The Peptides;" Vol. 1, Academic Press, New York, 1965, pp. 77–128. Examples of the activated form of the terminal carboxyl are the acid chloride, acid bromide, anhydride, azide, activated ester or O-acyl urea of a dialkylcarbodiimide. Preferred activated forms of the carboxyl are the acid chloride, or the 1-benzotriazolyl, 2,4,5-trichlorophenyl or succinimido activated esters.

Returning to the flow diagram again, the amidoester of formula VI is reacted under anhydrous conditions with about two to five molar equivalents of phosphorus pentasulfide under the conditions described above for the cyclization of the starting material of formula III with phosphorus pentasulfide. In this manner the corresponding thioacylaminoacid ester of formula VII is obtained.

Thereafter, the latter ester is hydrolyzed with a hydrolyzing agent to give the starting material of formula II. A preferred method of hydrolysis involves subjecting the ester of formula VII to the action of a strong base, for example, sodium hydroxide or potassium hydroxide, in the presence of sufficient water to effect hydrolysis of the ester. The hydrolysis is performed using a suitable solvent, for example, methanol, ethanol or 2-methoxyethanol. The reaction mixture is maintained at a temperature of from about 25° to 100° C., or at the reflux temperature of the solvent employed, until hydrolysis occurs. Usually ten minutes to six hours is sufficient for this hydrolysis.

The starting material of formula III, which is a des-(N-lower alkyl) derivative of the above noted amidoester of formula VI is prepared by coupling the compound of formula IV with a glycine lower alkyl ester in the same manner as described previously for the coupling of compounds IV and V.

The following examples further illustrate this invention.

EXAMPLE 1

2-(5-Bromo-1-naphthalenyl)-5-hydroxy-3-methylthiazolium hydroxide, inner salt (Ia; $R^1=CH_3$, $R^2=5—Br$ and $R^3=H$)

A solution of N-[(5-bromo-1-naphthalenyl)thioxomethyl]-N-methylglycine (338 mg, 1 mmole), described in Example 32 of said U.S. patent application Ser. No. 321,306, in acetic anhydride-triethylamine (1:1, v/v, 4 ml) was stirred at 20°–22° C. for 20 min. The reaction mixture was cooled in a refrigerator (4° C.) for 2 hr. The precipitate was collected and washed with cold diethyl ether, giving the title compound (200 mg); mp 180°–182° C.; NMR (DMSO-$d_6$) δ 3.45 (s, 3H), 6.40 (s, 1H), 7.75 (m, 6H); IR (white mineral oil) 1615, 1600 cm$^{-1}$; UVλmax (MeOH) 345 nm (ε 9,415), 294 (6,660), 218 (55,910).

By following the procedure of this example but replacing N-[(5-bromo-1-naphthalenyl)thioxomethyl]-N-methylglycine with an equivalent amount of another compound of formula II, the corresponding compounds of formula Ia are obtained.

For example, replacement with N-[[5-(trifluoromethyl)-6-methoxy-1-naphthalenyl]thioxomethyl]-N-methylglycine, described in said U.S. patent application, gave 5-hydroxy-2-[5-(trifluoromethyl)-6-methoxy-1-naphthalenyl]-3-methylthiazolium hydroxide, inner salt (Ia; $R^1=CH_3$, $R^2=5—CF_3$ and $R^3=6—CH_3O$); mp 166°–168° C.; NMR (DMSO-$d_6$) δ 3.50 (s, 3H), 4.00 (s, 3H), 6.40 (s, 1H), 7.80 (m, 5H); IR (white mineral oil) 1600, 1160, 1125 cm$^{-1}$; UVλmax (MeOH) 339 nm (ε

11,060), 296 (5,500), 284 (5,630), 274 (4,785), 227 (50,430).

Likewise, replacement with N-[(5-iodo-6-methoxy-1-naphthalenyl)thioxomethyl]-N-methylglycine, described in said U.S. patent application, gives 2-(5-iodo-6-methoxy-1-naphthalenyl)-5-hydroxy-3-methylthiazolium hydroxide, inner salt.

Likewise, replacement with N-[(3-chloro-4-methoxy-1-naphthalenyl)thioxomethyl]-N-methylglycine, described in said U.S. patent application, gives 2-(3-chloro-4-methoxy-1-naphthalenyl)-5-hydroxy-3-methylthiazolium hydroxide, inner salt.

EXAMPLE 2

2-(3-Chloro-4-methoxy-1-naphthalenyl)-5-ethoxythiazole (Ib: $R^2=3$—Cl, $R^3=4$—CH$_3$O and $R^4=OC_2H_5$)

A mixture of N-[(3-chloro-4-methoxy-1-naphthalenyl)carbonyl]glycine ethyl ester (4.0 g, 12.4 mmoles), described in the previously noted U.S. patent application Ser. No. 321,306, phosphorus pentasulfide (3.32 g, 14.92 mmoles) and dry pyridine (25 ml) was heated at reflux temperature for 45 min. The mixture was poured into warm water (300 ml, at about 50° C.). The diluted mixture was cooled in an ice bath, and then extracted with chloroform (2×50 ml). The extract was washed successively with 1 N aqueous HCl and brine, dried (Na$_2$SO$_4$), and concentrated to dryness to give 1.5 g of a mixture of the title compound and a byproduct, N-[(3-chloro-4-methoxy-1-naphthalenyl)thioxomethyl]glycine ethyl ester.

The preceding mixture (1.5 g) was dissolved in 1 N aqueous NaOH (15 ml) and methanol (100 ml). The resulting solution was stired at 20°–22° C. for 20 hr and evaporated to dryness. The residue was triturated with water. The insoluble material was collected by filtration and recrystallized from ethanol to give the title compound (2.2 g); mp 67°–68° C.; NMR (CDCl$_3$) δ 1.45 (t, J=7 Hz, 3H), 4.0 (s, 3H), 4.15 (q, J=7 Hz, 2H), 7.2 (s, 1H), 7.55 (m, 3H), 8.1 (m, 1H), 8.7 (m, 1H); IR (CHCl$_3$) 1525, 1573 cm$^{-1}$; UVλmax (MeOH), 320 nm (ε 10,300), 231 (34,200), 214 (25,200); Anal. Calcd for C$_{16}$H$_{14}$ClNO$_2$S: C, 60.09% H, 4.41% N, 4.38%; Found: C, 60.67% H, 4.38% N, 4.50%. The corresponding acid of the byproduct was isolated by rendering the above filtrate acidic and then extracting the filtrate with ethyl acetate.

By following the procedure of this example but replacing N-[3-chloro-4-methoxy-1-naphthalenyl)carbonyl]glycine ethyl ester with an equivalent amount of another starting material of formula III, other compounds of formula Ib are obtained. For example, replacement with N-[(5-bromo-1-naphthalenyl)carbonyl]glycine methyl ester gives 2-(5-bromo-1-naphthalenyl)-5-methoxythiazole. Similarly, replacement with N-[[5-(trifluoromethyl)-6-methoxy-1-naphthalenyl]carbonyl]glycine methyl ester gives 2-[5-(trifluoromethyl)-6-methoxy-1-naphthalenyl]-5-methoxythiazole.

We claim:

1. A compound of formula I

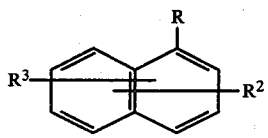

(I)

wherein R is

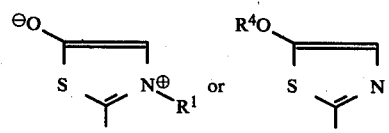

wherein $R^1$ is lower alkyl; $R^2$ is a halo substituent on the naphthalene ring and $R^3$ is hydrogen, or $R^2$ and $R^3$ each is a substituent at positions 3, 4, 5 or 6 of the naphthalene ring selected from the group consisting of lower alkoxy, trihalomethyl and halo; and $R^4$ is lower alkyl.

2. The compound of claim 1, represented by formula Ia

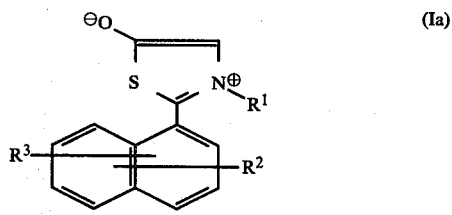

(Ia)

wherein $R^1$ is lower alkyl; $R^2$ is 5-halo and $R^3$ is hydrogen, or $R^2$ and $R^3$ are a pair of substituents on the naphthalene ring, the pair being selected from the group of pairs consisting of 3-halo-4-lower alkoxy, 5-halo-6-lower alkoxy and 5-(trifluoromethyl)-6-lower alkoxy.

3. The compound of formula Ia, as claimed in claim 2, wherein $R^1$ is lower alkyl, $R^2$ is 5-trifluoromethyl and $R^3$ is 6-lower alkoxy.

4. The compound of claim 1, which is 2-(5-bromo-1-naphthalenyl)-5-hydroxy-3-methylthiazolium hydroxide, inner salt.

5. The compound of claim 1, which is 5-hydroxy-2-[5-(trifluoromethyl)-6-methoxy-1-naphthalenyl]-3-methylthiazolium hydroxide, inner salt.

6. The compound of claim 1, represented by formula Ib

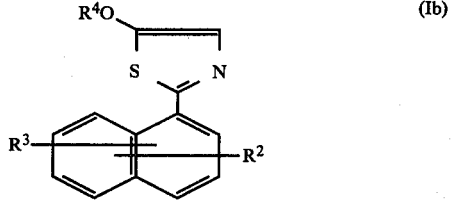

(Ib)

wherein $R^2$ is 5-halo and $R^3$ is hydrogen or $R^2$ and $R^3$ are a pair of substituents on the naphthalene ring, the pair of substituents being selected from the group of pairs consisting of 3-halo-4-lower alkoxy, 5-halo-6-lower alkoxy and 5-(trifluoromethyl)-6-lower alkoxy; and $R^4$ is lower alkyl.

7. The compound of formula Ib, as claimed in claim 6, wherein $R^2$ is 3-halo, $R^3$ is 4-lower alkoxy and $R^4$ is lower alkyl.

8. The compound of claim 1, which is 2-(3-chloro-4-methoxy-1-naphthalenyl)-5-ethoxythiazole.

9. A pharmaceutical composition for preventing or relieving neuropathy, nephropathy, retinopathy or cataracts in a diabetic mammal, which comprises an alleviating or prophylactic amount of a compound of claim 1 and a pharmaceutically acceptable carrier.

10. A method of preventing or relieving neuropathy, nephropathy, retinopathy or cataracts in a diabetic mammal, which comprises administering to said mammal an alleviating or prophylactic amount of a compound of claim 1.

* * * * *